United States Patent [19]
DiBernardo et al.

[11] Patent Number: 5,344,011
[45] Date of Patent: Sep. 6, 1994

[54] PACKAGING SYSTEM FOR AN ELONGATED FLEXIBLE PRODUCT

[75] Inventors: Dinah K. DiBernardo, San Jose; Kenneth L. Osborn; Ruth M. Fricker, both of Mountain View, all of Calif.

[73] Assignee: Advanced Cardiovascular Systems, Inc., Santa Clara, Calif.

[21] Appl. No.: 17,029

[22] Filed: Feb. 12, 1993

[51] Int. Cl.⁵ ............................................. B65D 85/671
[52] U.S. Cl. .................................... 206/364; 206/389; 242/172
[58] Field of Search ............... 206/363, 364, 389, 438, 206/570; 242/172

[56] References Cited

U.S. PATENT DOCUMENTS

| | | | |
|---|---|---|---|
| 3,633,758 | 1/1972 | Morse et al. | 306/364 X |
| 4,262,800 | 4/1981 | Nethercutt | 206/364 |
| 4,607,746 | 8/1986 | Stinnette | 242/172 X |
| 4,850,438 | 7/1989 | Charvin | 206/438 X |
| 4,925,448 | 5/1990 | Bazaral | 206/364 X |

*Primary Examiner*—Paul T. Sewell
*Assistant Examiner*—Beth Anne C. Cicconi
*Attorney, Agent, or Firm*—Crosby, Heafey, Roach & May

[57] ABSTRACT

A compact packaging system for elongated flexible products, such as catheters, guidewires and the like which keeps the products in a sterile environment until they are used but which allows preparation of the product for subsequent use. The system includes a housing with a main portion and a movable portion. The main portion has a plurality of passageways which receive the elongated product and a catch which releasably secures an elongated product within the housing passageways. The movable housing portion is adapted to expose a portion of the elongated product within the housing to facilitate its preparation for subsequent use.

10 Claims, 2 Drawing Sheets

PACKAGING SYSTEM FOR AN ELONGATED FLEXIBLE PRODUCT

BACKGROUND OF THE INVENTION

This invention generally relates to a packaging system for flexible elongated articles and particularly for sterilized elongated articles such as dilatation catheters and guidewires for percutaneous transluminal coronary angioplasty (PTCA).

In PTCA procedures, a guiding catheter having a preshaped distal tip is percutaneously introduced into the cardiovascular system of a patient and advanced therein until the preshaped distal tip thereof is disposed within the aorta adjacent the ostium of the desired coronary artery. The guiding catheter is twisted or torqued from the proximal end to turn the distal tip of the guiding catheter so that it can be guided into the thereof is introduced into and advanced through the guiding catheter to the distal tip thereof and then out of the distal tip of the guiding catheter until the balloon on the distal extremity of the dilatation catheter is properly positioned across the lesion. Once properly positioned, the flexible, relatively inelastic balloon is inflated to a predetermined size with radiopaque liquid at relatively high pressures (e.g., 4–12 atmospheres) to dilate the stenosed region of the diseased artery. The balloon is then deflated so that the dilatation catheter can be removed from the dilated stenosis and blood flow can then be resumed therethrough. With over-the-wire and rapid exchange type dilatation catheters, they are advanced out of the guiding catheter over a previously positioned guidewire to the desired location within the patient's coronary anatomy. With fixed wire catheters the guiding member is fixed within the catheter so both are advanced together out the distal end of the guiding catheter to the desired location within the coronary arteries of the patient.

Before a balloon dilatation catheter is inserted into the patient, liquid, such as the radiopaque liquid used for inflating the balloon, is injected into the catheter in order to vent entrapped air from the interior of the catheter. The entrapped air may be vented through a venting tube such as described in U.S. Pat. No. 4,323,071 (Simpson et al.) or through a venting passageway such as described in U.S. Pat. No. 4,692,200 (Powell) and U.S. Pat. No. 4,821,22 (Miller et al.) which are incorporated herein by reference. For the venting to be successful, the catheter must usually be manipulated to guide the bubbles of entrapped air within the catheter into a position adjacent to the venting means to allow the entrapped air to pass through the venting means. While the catheter is being manipulated during the venting procedure, care must be exercised to ensure that the sterility of the catheter is not compromised by the catheter contacting a non-sterile surface. Even after the catheter has been vented, the catheter, which is over three feet long, must be placed in a sterile environment until it is used in the angioplasty procedure. This typically involves laying the catheter over the draped surgical site on the patient. However, while the draped surgical site is sterile, it is not uncommon for the vented dilatation catheter to come into contact with a non-sterile surface, requiring discarding the vented catheter and prepping another dilatation catheter for the angioplasty. This replacement is expensive and inconvenient for the physician because then the replacement catheter itself must be vented to remove entrapped air.

What has been needed and heretofore unavailable is a packaging system which allows the catheter or other elongated device to be prepped and stored in a sterile environment with little risk of contact with a non-sterile surface prior to use. The present invention satisfies this and other needs.

SUMMARY OF THE INVENTION

This invention is directed to a packaging system for elongated products and particularly elongated products which are stored in a sterile condition.

The packaging system generally comprises a housing with a plurality of passageways which are adapted to receive an elongated product and hold the product in a coiled condition. The housing has means to expose at least part of the elongated product contained within the housing. In one embodiment of the invention a portion of the housing is slidable with respect to the other to expose the distal end of an elongated product held within the housing. In another preferred embodiment a wall of the housing is removable to expose the distal end of an elongated product within the housing. Preferably, the housing has a coiled tubular sheath disposed within the passageways in the housing which has an inner lumen which slidably receives the elongated product and holds the product into a coiled condition as the elongated product is advanced within she inner lumen of the tubular sheath. A means is provided to releasably secure the elongated product within the housing so as to prevent accidental removal from the housing.

A presently preferred embodiment of the invention is specifically directed to packaging intravascular products, particularly balloon angioplasty catheters. The balloon dilatation catheter can be filled with inflation fluid while the catheter is disposed within the housing to vent air from the catheter before it is advanced within the patient. The movable portion of the housing allows the distal portion of the dilatation catheter having the balloon to be exposed. The catheter is manipulated within the housing so as to drive entrapped air to the interior of the balloon where the venting means for catheter are located to vent the entrapped air.

The packaging system of the invention can also be employed to store guidewires. The movable portion of the housing allows the distal portion of the guidewire to be exposed so that the physician can manually shape the distal end of the guidewire before the guidewire is removed from the package and introduced into the patient.

The packaging system of the invention is more compact and is formed of much fewer components than existing dilatation catheter and guidewire packaging systems.

These and other advantages of the invention will become more apparent from the following detailed description of the invention when taken in conjunction with the accompanying exemplary drawings.

DETAILED DESCRIPTION OF THE INVENTION

Figure 1:
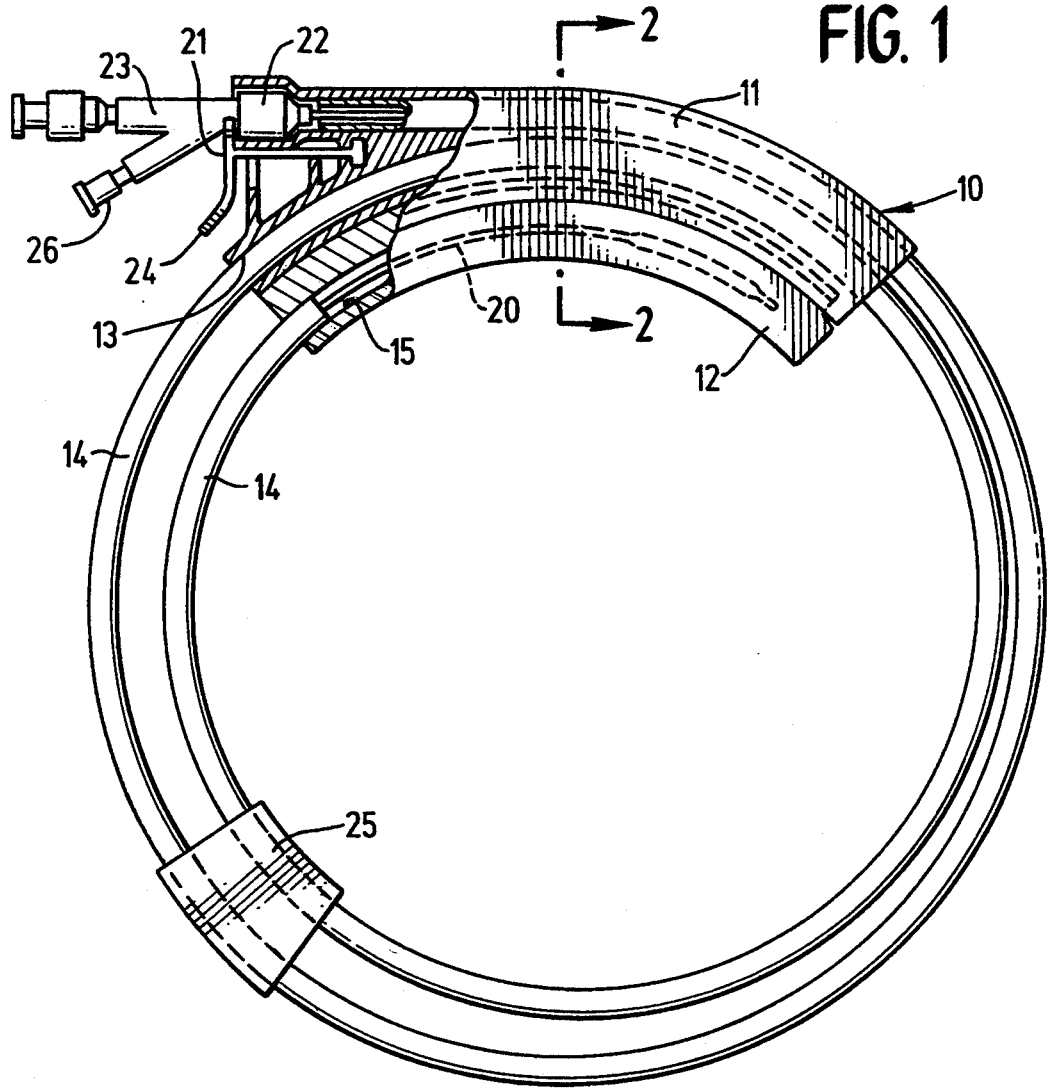
FIG. 1 is an elevational view, partially in section, of a packaging system embodying features of the invention.
Figure 2:
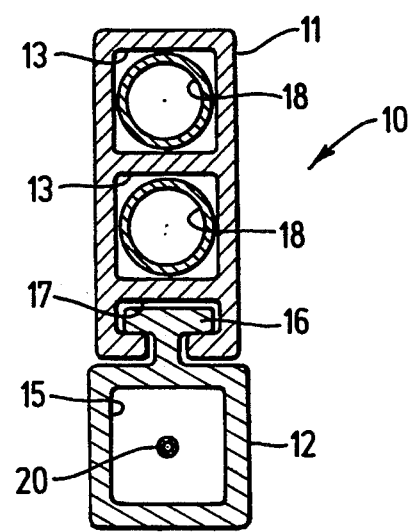
FIG. 2 is a transverse cross-sectional view of the packaging system shown in FIG. 1 taken along the lines 2—2.

A presently preferred embodiment of the invention is shown in FIGS. 1 and 2. As depicted in these drawings, the packaging system includes a housing 10 with a main portion 11 and a movable portion 12. The main portion of the housing has a plurality of arcuate passageways 13 which receive at least the proximal portion of a tubular sheath 14 and the movable portion has an arcuate passageway 15 which receives the distal end of the tubular sheath 14. The arcuate passageway 15 is dimensioned so that the movable housing portion 12 is slidable over the distal end of tubular sheath 14. The movable portion 12 has a T-shaped extension 16 which is slidably positioned within a T-shaped slot 17 provided in the main housing portion 11. The tubular sheath 14 has an inner lumen 18 which receives the dilatation catheter 20.

A trigger-like catch 21 is provided on the main housing portion 11 which has a U-shaped connecting portion which engages the lip of the nose piece 22 of the adapter 23 on the proximal end of the dilatation catheter 20. Finger pressure on the lever 24 will disengage the U-shaped connecting portion of catch 21 and release the catheter 20 and allow it to be removed from the packaging system.

Figure 3:
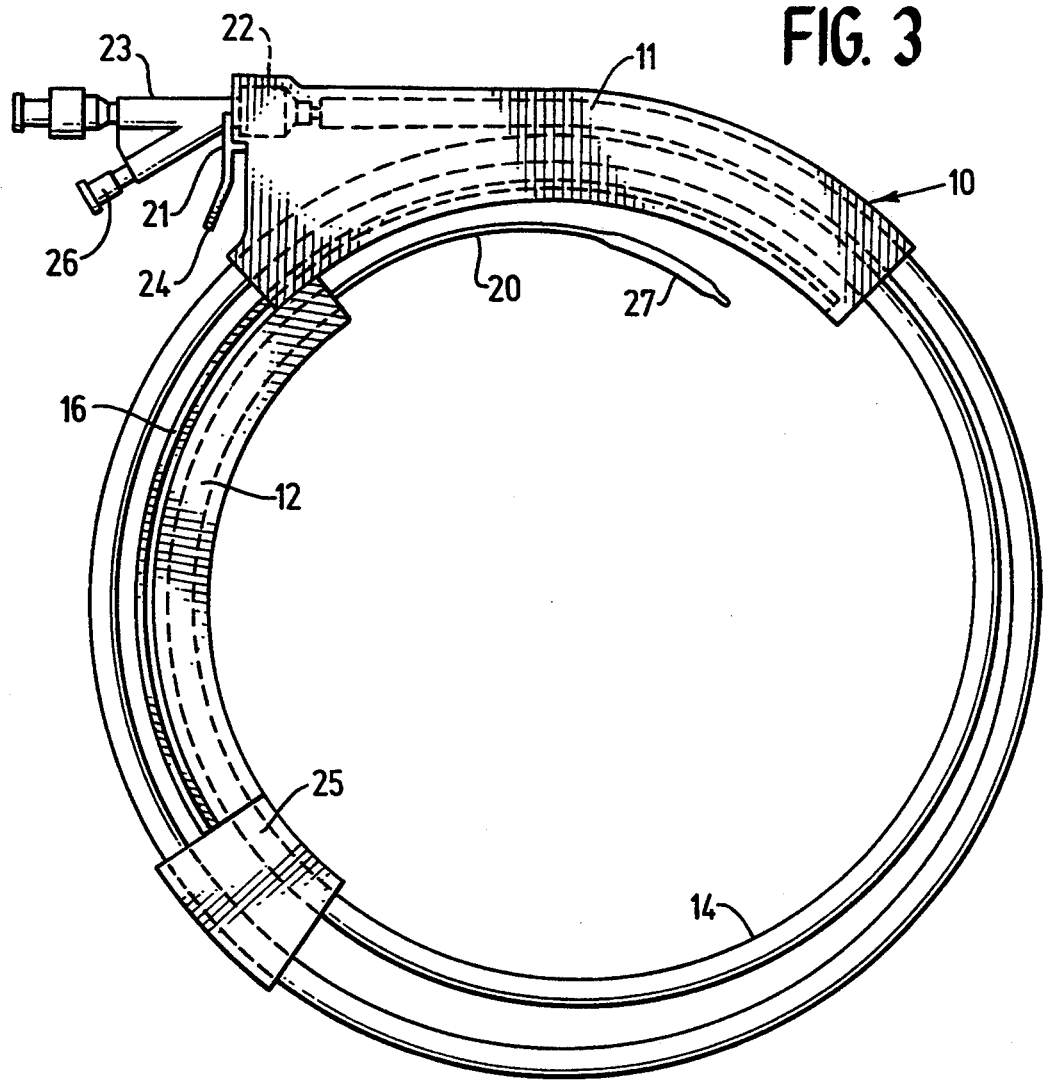
FIG. 3 is a view of the packaging system shown in FIG. 1 with the lower portion of the housing slidably moved counter-clockwise so as to expose the distal portion of a dilatation catheter disposed within the packaging system.

As shown in FIG. 3 movement of the movable housing section 12 in a counter clock-wise direction exposes the distal end of the catheter 20. A stopping element 25 is mounted on the coiled tubular sheath 14 to control the counter-clockwise movement of the movable housing portion 12 so that the T-shaped extension 16 on the movable portion is not pulled out of the T-shaped slot 17 in the main housing portion 11. Inflation liquid may be introduced into the interior of the catheter through the arm 26 of the adapter 23 to drive entrapped air within the catheter into the balloon 27 where it is vented to the atmosphere through a venting means (not shown). The venting means can be a small passageway which allows air but not liquid to pass such as described in U.S. Pat. No. 4,692,200 (Powell) and U.S. Pat. No. 4,821,22 (Miller et al.) or a vent tube such as described in U.S. Pat. No. 4,323,071 (Simpson et al.). With the distal portion of the catheter 20 being exposed, the venting of the entrapped air, which accumulates in the balloon 27, is observable without removing the catheter from the housing 10 and tubular sheath 14. When the venting procedure is completed, the inflation liquid can be removed, the balloon rewrapped if necessary and the movable housing portion 12 may then be moved clockwise to ensure that the distal portion of the catheter 20 is maintained in a sterile environment until it is time to remove the catheter from the package.

Figure 4:
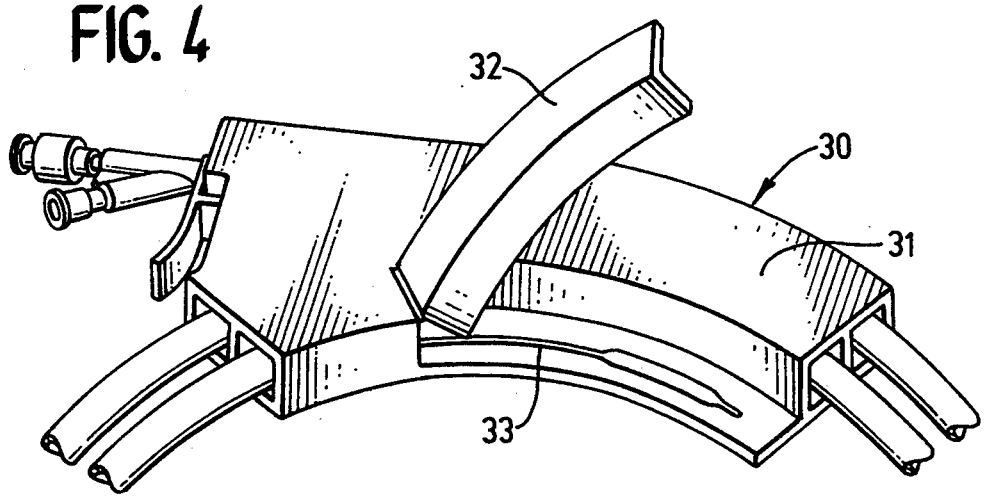
FIG. 4 is an elevational view, partially in section, of an alternate packaging system similar to that shown in FIG. 1 but having a liftable housing section for exposing the distal portion of a catheter disposed therein.

FIG. 4 illustrates an alternative embodiment of the invention in which housing 30 has a main portion 31 and a movable portion 32 which is hinged to the main portion so as to swing away from the main portion as shown in the drawing. When the movable portion 32 is swung away from the main portion 31, the distal portion of catheter 33 is exposed which allows for the monitoring of the venting procedures as described above for the first described embodiment. All of the other features of this embodiment are the same as that shown in FIGS. 1 and 2.

The various components of the invention can be formed of suitable plastic materials such as polyethylene, polycarbonate, polyvinyl chloride, polyurethane and the like. If desired, the components may be formed of metal or metal alloys. In a presently preferred embodiment the housing is formed of Lexan® 1210, a polycarbonate from the General Electric Company, and the tubular sheath is formed of a high density polyethylene.

While the invention has been described herein primarily in terms of a packaging system for dilatation catheters, those skilled in the art will recognize that it may be utilized to hold other types of catheters, guidewires and other elongated products in a sterile environment until they are used. Other modifications and improvements can be made to the invention without departing from the scope of the invention.

What is claimed is:

1. A packaging system for an elongated flexible product in a coiled condition having more than one complete turn, comprising a housing which has a main portion and a movable portion connected to the main portion and a plurality of separate passageways within the housing which receive a coiled elongated flexible product, the movable portion of the housing being movably connected to the main housing portion to facilitate exposure of only a small distal portion of an elongated flexible product disposed within the passageways; and an elongated tubular sheath which has at least in part an arcuate shape, which has at least proximal and distal portions disposed within the passageways of the housing and which has an inner luman configured to slidably receive an elongated flexible product therein.

2. The packaging system of claim 1 wherein the housing passageways are arcuate in shape.

3. The packaging system of claim 1 wherein the movable portion of the housing is slidably connected to the main portion of the housing so that, when the movable portion of the housing is moved with respect to the main portion of the housing, a distal portion of an elongated flexible product disposed within the passageways is exposed.

4. The packaging system of claim 1 wherein the main portion of the housing has means to releasably secure a proximal portion of an elongated flexible member disposed within the housing.

5. The packaging system of claim 4 wherein means is provided to stop movement of the movable portion of the housing to prevent complete disengagement of the movable portion of the housing from the main portion of the housing.

6. The packaging system of claim 1 wherein the elongated tubular sheath is shorter than the elongated flexible member disposed within the inner lumen of the tubular sheath so that a distal portion of the elongated flexible member will be exposed when the movable portion of the housing is moved.

7. The packaging system of claim 1 wherein the main portion of the housing has a plurality of passageways which receive a turn of the coiled sheath.

8. A packaging system for a sterilized balloon dilatation catheter in a coiled condition having more than one complete turn, comprising:

a housing which has a main portion ad a movable portion connected to the main portion and a plurality of separate passageways which receive a coiled dilatation catheter, the movable portion of the housing being movably connected to the main housing portion to facilitate exposure of only a small distal portion of a dilatation catheter having a dilatation balloon within the passageways; and an elongated tubular sheath which has at least in part an arcuate shape, which has at least proximal and distal portions in communication with the passageways of the housing and which has an inner lumen configured to slidably receive a dilatation catheter.

9. The packaging system of claim 8 wherein the movable portion of the housing is slidably mounted tot he main portion of the housing so that, when the movable portion of the housing is moved with respect to the main portion of the housing, the distal portion of the dilatation catheter having a dilatation balloon arcuate passageways is exposed.

10. The packaging system of claim 8 wherein the main portion of the housing has means to releasably secure an adapter mounted on a proximal end of the dilatation catheter disposed within the housing.

* * * * *

UNITED STATES PATENT AND TRADEMARK OFFICE
CERTIFICATE OF CORRECTION

PATENT NO. : 5,344,011

DATED : September 6, 1994

INVENTOR(S) : Dinah K. DiBernardo et al.

It is certified that error appears in the above-identified patent and that said Letters Patent is hereby corrected as shown below:

Col. 5, claim 8, line 4, change "ad" to --and--.

Col. 6, claim 9, line 2, change "tot he" to --to the--.

Signed and Sealed this

Seventh Day of March, 1995

*Attest:*

BRUCE LEHMAN

*Attesting Officer*         *Commissioner of Patents and Trademarks*